United States Patent [19]
Breimesser et al.

[11] Patent Number: 5,427,106
[45] Date of Patent: Jun. 27, 1995

[54] ULTRASOUND TRANSDUCER DEVICE WITH A ONE-DIMENSIONAL OR TWO-DIMENSIONAL ARRAY OF TRANSDUCER ELEMENTS

[75] Inventors: Fritz Breimesser, Nürnberg; Bernd Gromoll, Baiersdorf; Hans-Peter Heindel, Fürth; Bertram Sachs, Erlangen, all of Germany

[73] Assignee: Siemens Aktiengesellschaft, München, Germany

[21] Appl. No.: 279,932

[22] Filed: Jul. 25, 1994

[30] Foreign Application Priority Data

Jul. 26, 1993 [DE] Germany ............ 43 25 028.9

[51] Int. Cl.$^6$ .............................................. A61B 8/00
[52] U.S. Cl. .............................. 128/661.01; 310/326
[58] Field of Search ................... 128/660.01, 661.01, 128/662.03; 73/628, 625, 641; 367/7; 310/326, 327, 346, 358

[56] References Cited

U.S. PATENT DOCUMENTS

| | | | |
|---|---|---|---|
| 3,937,066 | 2/1976 | Green et al. | 73/607 |
| 4,672,591 | 6/1987 | Breimesser et al. | 367/152 |
| 5,229,933 | 7/1993 | Larson, III | 128/660.01 |

FOREIGN PATENT DOCUMENTS

| | | |
|---|---|---|
| 3021449 | 12/1981 | Germany . |
| 3501808 | 4/1989 | Germany . |
| 2052918 | 1/1981 | United Kingdom . |

OTHER PUBLICATIONS

Ultrasonics, Mar. 1981, pp. 81–86, M. Pappalardo: *Hybrid linear and matrix acoustic arrays*.
Proceedings of the IEEE, vol. 67, No. 4, Apr. 1979, James F. Havlice et al.: *Medical Ultrasonic Imaging: An Overview of Principles and Instrumentation*, pp. 620–641.
Ultrasonic Imaging 14 (1992), pp. 213–233, S. W. Smith et al.: *Two-Dimensional Arrays for Medical Ultrasound*.
IEEE Transactions on Ultrasonics, Ferroelectrics, and Frequency Control, vol. 38, No. 4, Jul. 1991; Daniel H. Turnbull et al.: *Beam Steering with Pulsed Two-Dimensional Transducer Arrays*, pp. 320–333.

*Primary Examiner*—George Manuel
*Attorney, Agent, or Firm*—Kenyon & Kenyon

[57] ABSTRACT

An ultrasound transducer device with a one-dimensional or two-dimensional array of transducer elements ($4_j$) has at least one plate-shaped component. This component contains an acoustical attenuation element (3), at one narrow side (3c) of which the transducer elements ($4_j$) are arranged with piezoelectric oscillation elements and electrodes, as well as an electronic circuit part (17a) and connection leads (10a) between this circuit part and the electrodes. An electrode is arranged at each transducer element ($4_j$) between its oscillation element and the attenuation element (3), which has a connection part for the connection leads (10a) which leads to a broad side (3a), and a strip-shaped carrier element (14) is connected with the attenuation element (3), with the electronic circuit (17a) located on the one broad side. Cooling channels (20, 21) may be used as a means for cooling the carrier element (14, $14_k$). Preferably, two components can form a common partial system (2) of the transducer device.

19 Claims, 3 Drawing Sheets

ULTRASOUND TRANSDUCER DEVICE WITH A ONE-DIMENSIONAL OR TWO-DIMENSIONAL ARRAY OF TRANSDUCER ELEMENTS

BACKGROUND OF THE INVENTION

The present invention relates to an ultrasound transducer device with a one-dimensional or two-dimensional array of transducer elements.

An ultrasound transducer device is disclosed in the publication "Ultrasonics", March 1981, pages 81 to 86, and in Patent Document No. GB-A-2,052,918.

In the field of ultrasound imaging technology, a body to be examined, especially a human body, is exposed to ultrasonic waves using ultrasound pulses. An ultrasound image is built up from ultrasound echo pulses reflected at the border surfaces of this body, using an electronic signal processing unit, with the echo amplitudes and the echo run times serving as data. For example, such a method is disclosed in "Proc. IEEE", Vol. 67, No. 4, April 1979, pages 620 to 641. To send and receive the ultrasound pulses according to such a pulse-echo method, piezoelectric transducer elements are preferably used. These transducer elements can be arranged in a linear (one-dimensional) row or chain (a so-called linear array) and are controlled by an electronic control unit, separately or in groups, to achieve a directing effect. The control of the sonic beam takes place by time-delayed transmission of the individual elements in the transmission case, where the desired beam direction results from superimposition of the waves proceeding from the elements, pursuant to Huygens' principle. In the reception case, the desired angle-dependent sensitivity is also achieved by time-dependent or phase-dependent superimposition of the time signal progressions recorded by the individual elements. Corresponding arrays of ultrasound transducer elements are therefore also referred to as "phased arrays."

Using such phase-delayed controlled linear arrays, ultrasound beams that can be pivoted and focused in a plane formed by the normal line on the array surface and the longitudinal direction of the array can be sent and received. The pivot angle measured relative to the normal line for the ultrasound beam increases as the distance between the transducer elements decreases. This distance is generally selected to be approximately equal to half the wavelength $\lambda$ of the ultrasound, in order to suppress additional diffraction patterns in this way, and amounts to about 0.2 mm, for example, at a mean frequency of 3.5 MHz. On the other hand, a certain minimum length of the linear array is necessary, in order to achieve sufficient sonic amplitude and exact focusing of the beam. From these two requirements with regard to the reciprocal distance of the transducer elements and the minimum length of the array, a minimum number of transducer elements for the array is derived, which minimum number of elements is typically 64 or higher.

For any desired beam direction of an ultrasound beam in all three dimensions, which are a prerequisite for imaging moving bodies such as blood flow in the heart or arteries, the one-dimensional, linear array must be expanded to form a two-dimensional matrix (a so-called 2D array arrangement). Such a two-dimensional matrix array is disclosed, for example, in "Ultrasonics Imaging", Vol. 14, 1992, pages 213 to 233. Such matrix arrays for a three-dimensional beam control (e.g.,see "IEEE Trans. Ultrason., Ferroel., Frequ. Contr.", Vol. 38, No. 4, July 1991, pages 320 to 333) must fulfill certain conditions with regard to their lateral and axial resolution capacity, in order to be suitable for diagnostic purposes. While the axial resolution capacity is primarily determined by the frequency given off and the band width of the necessary electronics, the lateral resolution capacity is established by the frequency and the effective aperture of the array. For corresponding commercial ultrasound transducer devices, the following values are typical:

Mean frequencies: 3.5 to 10 MHz, effective aperture: 19 to 10 mm, band width: $\geq$50% (6 dB) with reference to the mean frequency.

If the resolution capacity which can be achieved with this is also used as a basis for 2D matrix arrays, then individual element distances of 0.2 to 0.075 mm and matrices of at least 64×64, particularly 100×100 elements, are obtained on the basis of the $\lambda/2$ conditions mentioned. These 10,000 elements must be housed on an area of 50 mm×50 mm, for example, with their sound-producing surfaces being approximately 0.2 mm×0.2 mm each. The thickness of the individual elements is 0.35 mm (for 3.5 MHz) to less than 0.2 mm (for 10 MHz), depending on the frequency and the piezo ceramics used. In addition, an over-response attenuation should reach about 30 dB between the individual elements and the electrical transmission and reception channels assigned to them, both acoustically and electronically. This requires significant efforts with regard to a suitable acoustic attenuation element, a so-called backing, and also with regard to insulation of the individual electrical supply lines. There can be no corresponding number of electronic transmission and reception channels to stand against the large number of individual elements. Therefore, effective utilization of the maximum possible number of channels is required, and can be achieved by means of multiplexer circuits. For both modes of operation (i.e., transmission and reception), electronic circuit parts are therefore required in the vicinity of the piezoelectric transducer elements. It is most practical to structure these circuit parts as integrated circuits, which are to be arranged on the acoustical shadow side of the transducer elements. In this connection, a high packing density of the elements leads to problems with regard to the contacting and structural technology, as well as with regard to the power dissipation of the electronic circuit parts.

From the "Ultrasonic" publication mentioned above and from Patent Document No. GB-A-2,052,918, an ultrasound transducer device with a plurality of ultrasound transducer elements is known, with the transducer elements being arranged in a two-dimensional matrix. Here, the transducer device is composed of several plate-shaped components. Each of these components contains a plate-shaped acoustic attenuation element, at the narrow side of which a one-dimensional row (line) of transducer elements is arranged. These transducer elements are formed by a corresponding subdivision of a strip-shaped piezoelectric element. For each of the oscillation elements of an element formed in this way, the two required electrodes are affixed at opposite side surfaces, so that the electrodes are aligned parallel to the sonic beam direction. The electrical connection leads connected to this run via the corresponding two broad sides of the attenuation element and lead to an electronic circuit pan affixed at the attenuation element. In the known embodiment, the circuit pan of each component of the transducer device is therefore composed of two circuit subunits located on the opposite broad sides of their attenuation element. On the basis of this bilateral arrangement of circuit subunits on each attenuation element, the packing density of the entire transducer device consisting of the individual components is therefore correspondingly limited. This restriction is also due to the fact that the electronic circuit parts on the attenuation element are not cooled and thus only a limited power dissipation of the electronics can be permitted. Furthermore, the structure provided for the known transducer device cannot be easily provided for higher frequencies and thus smaller dimensions of the elements, due to a minimum thickness of the silicon of over 0.1 mm. Furthermore, since the elements which emit sonic waves are each connected with the attenuation element only over part of the surface, at their lower part, this impairs their sonic wave emission behavior in disadvantageous manner.

SUMMARY OF THE INVENTION

The present invention structures the ultrasound transducer device with the characteristics stated above in such a way that a relatively simple structure of the transducer device with a high packing density of its transducer elements is made possible, particularly to form a two-dimensional matrix array, and problem-free operation of the device can be guaranteed. The requirements stated with regard to the resolution capacity should be fulfilled in this connection, at least for the most part.

According to an embodiment of the present invention, electrodes are arranged between the acoustical attenuation element and the oscillation element for each transducer part. The electrical connection part of each electrode is passed around an edge between a narrow side and an adjacent broad side of the acoustical attenuation element and connected with a related connection lead. A strip-shaped carrier element is attached at the narrow side of the acoustical attenuation element which faces away from the transducer elements. The strip-shaped carrier element contains the electronic circuit assigned to all of the transducer elements of the component on one broad side. A means for cooling the carrier element includes one or more cooling channels within the carrier element which contain a cooling medium.

In the transducer device according to the present invention, the connection leads which belong to one component and the electronic circuit part connected to them are arranged on only one broad side of this component. This makes it possible to achieve an increase in the packing density as compared with the known embodiment. Since the electronic circuit part is affixed on its own carrier element, particularly integrated into it, this element can be structured to have a large area, which is advantageous from a cooling technology and electrical or electronic point of view. Furthermore, minimal lengths of the connection leads must be guaranteed, so that they cause correspondingly low emission losses and are only subject to slight emission impact.

BRIEF DESCRIPTION OF THE DRAWINGS

Advantageous further developments of the transducer device according to embodiments of the present invention will become apparent from the following description in conjunction with the attached drawings.

In the figures, corresponding parts are designated with the same reference symbols.

DETAILED DESCRIPTION

An ultrasound transducer device according to an embodiment of the present invention, which is also referred to as an "applicator" or can be part of such an applicator, is composed of a certain number of plate-shaped components. It is advantageous that each component of the entire device can be produced and tested individually and then stacked to form the entire device. Each of these components should contain a one-dimensional row (line, chain) of ultrasound transducer elements arranged behind one another in a longitudinal direction, with this row particularly representing a column or a line of a generally rectangular, preferably square matrix arrangement of all the transducer elements of the device. Pursuant to a particularly preferred embodiment of the present invention, each of two adjacent components can be structured as a partial system with a double row of ultrasound transducer elements. A corresponding embodiment of such a partial system is shown in FIG. 1 as a slanted view.

Figure 1:
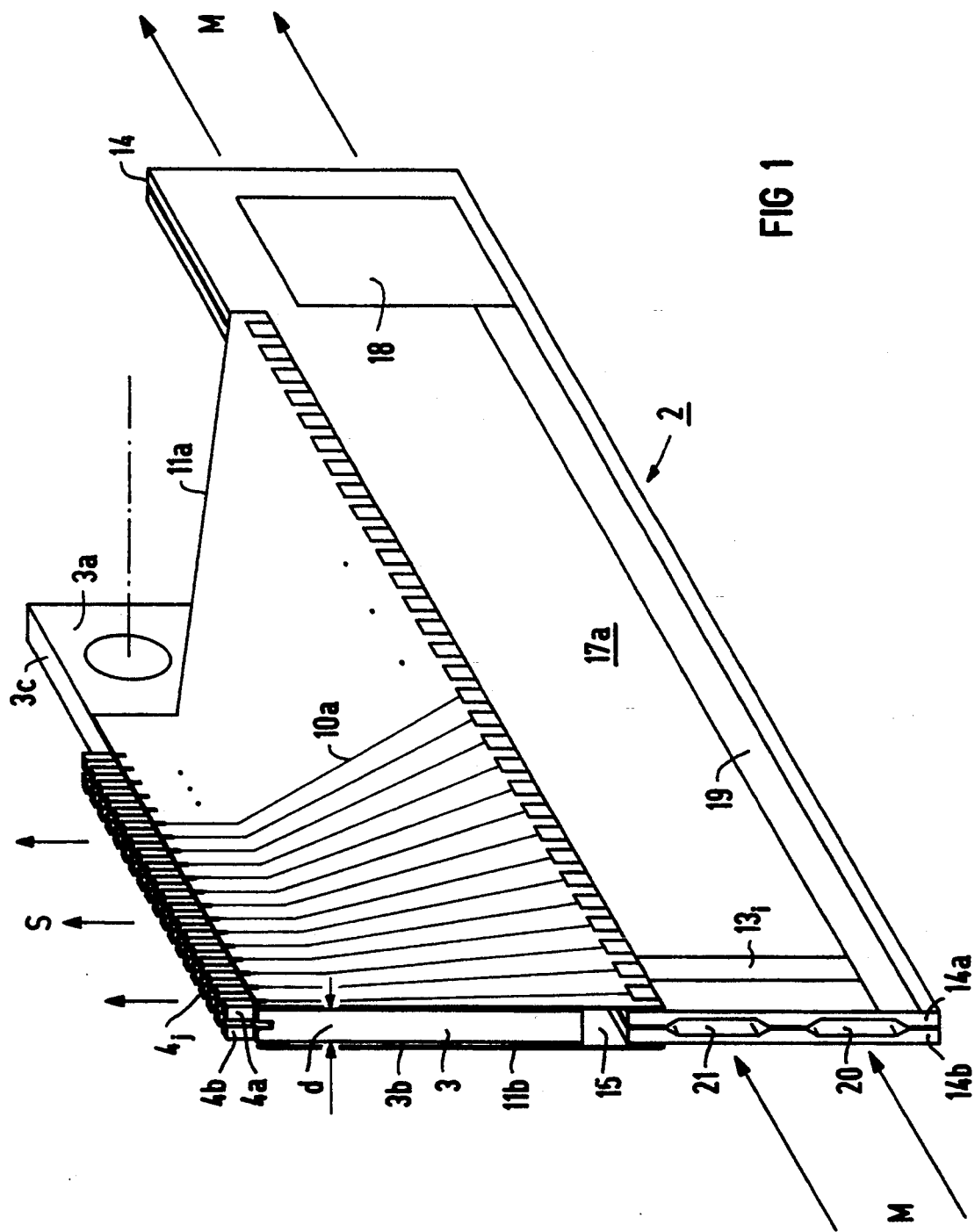
FIG. 1 illustrates a partial system of an ultrasound transducer device formed from two components according to an embodiment of the present invention.

The partial system 2 illustrated in FIG. 1 can be imagined as two components joined back to back, where individual parts of these components can also form common elements. The partial system 2 comprises an acoustic attenuation element 3, on the upper narrow side 3c of which two rows 4a and 4b of ultrasound transducer elements $4_j$ are arranged. Here, j=1, . . . M, with M being the total number of all transducer elements $4_j$ of the double row 4a–4b. For example, 2×64 such elements $4_j$ may be provided. The attenuation element 3 which serves as a backing for these transducer elements consists of a special epoxy resin, for example. Its thickness d is adapted to the corresponding lateral expanse of the double row 4a–4b.

Figure 2:
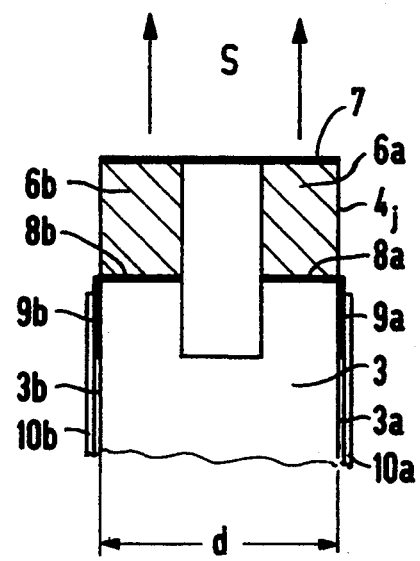
FIG. 2 illustrates two transducer elements of the partial system illustrated in FIG. 1.

Of this double row, two individual ones of these ultrasound transducer elements $4_j$, which are essentially all structured the same, are shown in a side view in FIG. 2. Each of these elements $4_j$ and $4_{j+1}$ contains a column-shaped or cube-shaped oscillation element 6a or 6b consisting of a piezoelectric material such as PZT. At the free end surfaces and at the opposite lower surfaces of the oscillation elements 6a and 6b which face the attenuation element 3, there are two electrodes 7 and 8a or 8b which are required for excitation of these elements, which are indicated by heavier lines. These electrodes, which consist of Ti-Au layers, for example, are thus directed perpendicular to the emission direction of the ultrasound beam S (i.e., the normal lines on the electrode surfaces point in this emission direction). As is furthermore indicated in FIG. 2, all the oscillation elements of a double row can be provided with a common, continuous electrode 7 on the end surface, for example glued on in the form of a foil. This electrode is generally applied to ground potential and is covered with a fitting layer, if necessary. The electrical connection of this electrode is located at the edge of the double row in this instance. The electrodes on the lower pan, 8a and 8b, each have an electrical connection part 9a or 9b. These connection parts lead around an edge between the upper narrow side 3c of the attenuation element 3 and the adjacent broad side 3a or 3b in each instance, and contact with an electrical connection lead 10a or 10b.

As is furthermore evident from FIG. 1, all of the connection leads 10a or 10b which belong to one row 4a or 4b and lead jointly over one of the broad sides 3a or 3b of the attenuation element 3 can be brought together into a flexible foil conductor 11a or 11b, for example made of lead wires embedded into or arranged on a polyimide, in the form of a flexible printed circuit. Each connection lead represents the electrical connection between the related transducer element $4_j$ and an electronic part $13_i$, within one channel i (with i=1, ... N, where N is the number of channels or transducer elements in a row, and thus N=M/2). In FIG. 1, only one electronic part $13_i$ belonging to one channel is illustrated, by means of the area of a corresponding carrier element 14 which it occupies. This carrier element is also plate-shaped or strip-shaped in structure, with its thickness corresponding, at least to a great extent, to the thickness d of the attenuation element 3. The carrier element 14 is mechanically attached to the lower narrow side of the attenuation element 3 with its upper narrow side, for example via the foil conductors 11a and 11b arranged at both sides of the attenuation element. For acoustical reasons, a narrow interstice 15 can remain between the two elements 3 and 14, if necessary. Since the area on the carrier element 14 which is occupied by the electronic parts $13_i$ generally takes up a larger expanse in the longitudinal direction (main direction of expanse) of the partial system 2 as compared with the corresponding expanse of the double row 4a-4b of transducer elements $4_j$, it is advantageous if each foil conductor 11a, 11b is structured to widen from the region of the transducer elements towards the region of the electronic parts.

The electronic part $13_i$ assigned within an electronic channel is generally designed both for transmission and reception. If necessary, however, it is also possible to provide separate electronic parts for these two modes of operation, for example with different technologies, where these parts can also be arranged behind each other. All of the electronic parts which belong to a row of transducer elements form at least one electronic circuit part. In this connection, the circuit part 17a is not shown in greater detail in FIG. 1, except for the electronic part $13_i$ which belongs to one channel. It is advantageous to integrate circuit part 17a into the carrier element 14, if the latter consists essentially of a material used in semiconductor technology, such as Si, which is suitable for such an integration. This circuit part 17a is advantageously located in the region of the acoustical shadow of the transducer device and is oriented perpendicular with reference to the sonic wave emission direction S. For the transducer series 4b, a corresponding electronic circuit part is to be provided on the rear broad side of the carrier element 14, which cannot be seen in FIG. 1. The connection of the electronic parts $13_i$ with each other and with a connection surface 18 is referred to as connection 19 in FIG. 1. The circuit part 17a is connected with subsequent electronics, particularly with a multiplexer, via connection surface 18 and connection 19.

In FIG. 1, in order to make the illustration more easily understood, the common ground electrode 7 on the end surface is not shown. However, the common ground electrode 7 is illustrated in FIG. 2 Common ground electrode 7 is contacted, for example, via the part of the area 3c not occupied by the double row 4a-4b. In addition, the drawing does not illustrate the representation of at least one shielding surface, which can serve for reciprocal electrical uncoupling or shielding of adjacent partial systems 2. This shielding surface, which is generally applied to ground potential, and is insulated with regard to adjacent electrically conductive parts, covers at least part of the region of the foil conductor 11a and can be structured to have so large an area, if necessary, that the electronic circuit part 17a is also covered. If needed, at least one such shielding surface can be provided on each of the two outside surfaces of the partial system 2.

As is furthermore indicated in FIG. 1, the carrier element 14 can advantageously be composed of two plate-shaped parts 14a and 14b, with their surfaces that face each other being structured in such a way that cooling channels 20 and 21 for a cooling medium M are formed. Using this cooling medium, dissipated heat generated by the electronic circuit parts can be removed. Each plate 14a and 14b can advantageously be a Si chip which is provided with the related circuit part 17a or 17b. Possibilities for structuring cooling channels in such chips are the object of German Patent Application No. DE-P 43 11 839.9 dated Apr. 15, 1993, which is not a prior publication, with the title "Mikrokühleinrichtung für eine Elektronik-Komponente" ["Microcooling device for an electronic component"], which is incorporated herein by reference.

Figure 3:
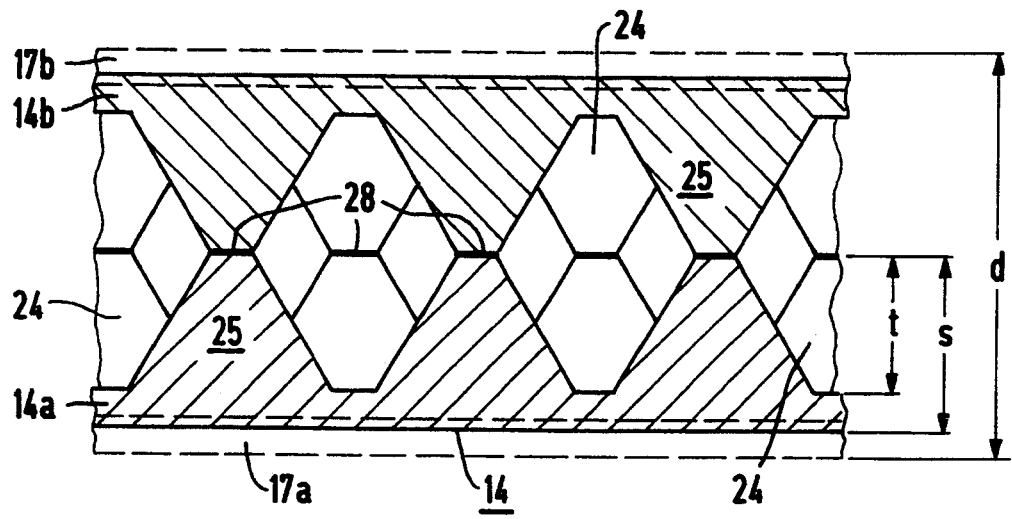
FIG. 3 illustrates a carrier element for electronic circuit parts of an ultrasound transducer device according to an embodiment of the present invention.

An embodiment of a carrier element 14 made of Si with two cooling channels 20 and 21 is shown in cross-section in FIG. 3. To structure this carrier element as a heat exchanger element to conduct away dissipated heat caused by the electronic circuit parts 17a and 17b, two thin strips or plates (chips) are required, which are structured in a corresponding manner, preferably in the same manner, at least at their surfaces that are joined together. The structuring of each Si plate is undertaken in a known manner, by working recesses into a flat side of the plate in question, which is generally level at first. This flat side represents the back of the plate with regard to the related electronic circuit part, which is only indicated with broken lines in FIG. 3. A correspondingly structured first Si plate 14a has a thickness s, for example, which together with the related electronic circuit element 17a is preferably approximately at least half as large as the thickness d of the acoustical attenuation element. In its one flat side, recesses 24 are anisotropically etched in such a manner that pyramid stumps 25 are obtained. These pyramid stumps are evenly distributed over the surface to be structured, and are arranged offset from one another, and are at equal distances from one another in the region of the lower parts. The depth t of the recesses 24, which corresponds to the height of the pyramid stumps 25, is less than the plate thickness s. A further Si plate 14b is structured corresponding to the first Si plate 14a. The two Si plates 14a and 14b are then joined at surfaces of their blunted pyramid tips and are connected together there to form a rigid heat exchanger element, using a special means of connection. In this way, because of the corresponding recesses in the two Si plates, cooling channels 27 are formed with relatively large flow cross-sections. As the means of connection 28 between the Si plates 14a and 14b, indicated in FIG. 3 by heavier lines, it is advantageous to use an adhesion agent or glue, preferably a silver conductive adhesive, which conducts heat well.

In the structuring of the Si plates, it is practical if web-like lateral end pieces are formed, which result in a trough shape of the structured Si plate 14a or 14b in each instance, seen in cross-section, and thus prevent lateral exit of a cooling medium M from the carrier element 14.

It is also possible to form a micro heat pipe system using the carrier element 14 composed of two plates. For this, the structure according to FIG. 3 is provided with end webs on all sides, and the interior space which can therefore be closed off on all sides is filled with a cooling fluid, for example with water or with a special fluorocarbon.

Figure 4:
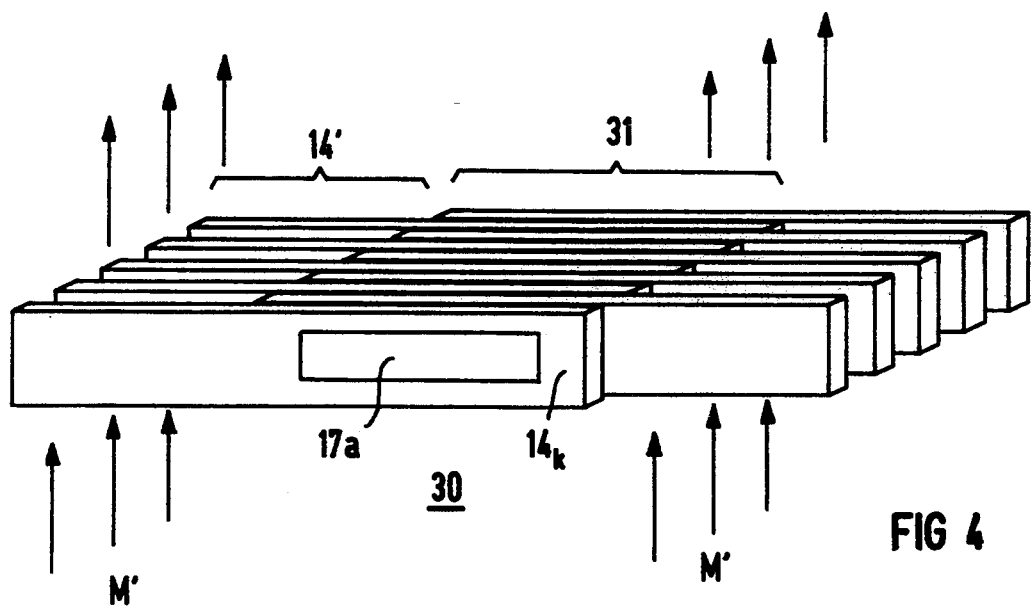
FIG. 4 illustrates an arrangement of several carrier elements as part of a transducer device according to an embodiment of the present invention.

Such heat pipe systems are assumed in an arrangement of several Si carrier elements, which are shown in a slanted view in FIG. 4. Corresponding to the number of rows or double rows of the array of transducer elements of the transducer device according to an embodiment of the present invention, the carrier element arrangement 30 has a number k of carrier elements $14_k$. Seen in the longitudinal direction of the transducer device, each carrier element extends not only over the heat-generating region illustrated by a surface 31 of the electronic circuit parts (17a, 17b) to be carried by it or integrated into it, but is further extended in this direction by a part 14'. By joining adjacent carrier elements $14_k$ in an offset manner, a comb-like structure can be achieved, with the reciprocally spaced extension parts 14' representing cooling ribs for a cooling medium M', such as ambient air, which flows past them on the outside. In order to support the transfer of heat to the ambient air, particularly at the extension parts 14' which form the cooling ribs, measures which enlarge the surface can furthermore be provided at the outside surfaces in each instance. The parts of the carrier elements $14_k$ which surround the regions which lie adjacent to each other and generate the heat are structured pursuant to FIG. 1. These regions 31 are connected with the other parts of the device component or partial system (2) in question.

Of course it is also possible to use carrier elements $14_k$ which are open on the side for the arrangement pursuant to FIG. 4, through which a cooling medium such as air can enter into the channel system of the carrier elements and again exit from this system.

The transducer device according to an embodiment of the present invention as described above includes a two-dimensional matrix array of transducer elements, and is composed of several components or partial systems. However, other embodiments of the present invention may be implemented without departing from the spirit and broad scope thereof. For example, the measures according to the present invention can also be used to couple the electronic circuit parts to the electrodes of the transducer elements and also for cooling in the case of linear (one-dimensional) arrays, which thus have only a single row of transducer elements.

What is claimed is:

1. An ultrasound transducer device with an array of transducer elements, the ultrasound transducer device including at least one plate-shaped component which each comprise:

a) an acoustical attenuation element;

b) a row of transducer elements arranged at a narrow side of the acoustical attenuation element, which transducer elements each have a piezoelectric oscillation element with electrodes arranged at opposite surfaces;

c) an electronic circuit portion assigned to the transducer elements; and d) connection leads between the electronic circuit portion and the electrodes of the transducer elements;

wherein said electrodes are arranged between the acoustical attenuation element and the oscillation element for each transducer element, the electrical connection part of each electrode passes around an edge between a narrow side and an adjacent broad side of the acoustical attenuation element and is connected with a related connection lead in each instance: and each said component further comprising:

a strip-shaped carrier element attached at the narrow side of the acoustical attenuation element which faces away from the transducer elements, which strip-shaped carrier element contains the electronic circuit portion assigned to all transducer elements of the component on one broad side; and a means for cooling the carrier element.

2. The ultrasound transducer device according to claim 1, wherein several of said plate-shaped components form a two-dimensional matrix array of transducer elements.

3. The ultrasound transducer device according to claim 2, wherein two components are integrated into a partial system of the transducer device, with two transducer elements forming a double row, and wherein the connection leads and electronic circuit portions which belong to the rows are located on opposite broad sides of the partial system.

4. The ultrasound transducer device according to claim 1, wherein connection leads which belong to a row of the transducer elements are formed by a flexible foil conductor.

5. The ultrasound transducer device according to claim 4, wherein the flexible foil conductor widens from a longitudinal expanse of the row of transducer elements toward a corresponding expanse of the electronic circuit portion.

6. The ultrasound transducer device according to claim 1, further comprising a shielding surface-on at least one outside surface of the component which covers at least a region of the connection leads.

7. The ultrasound transducer device according to claim 1, wherein the means for cooling of at least one carrier element comprises within the at least one carrier element one or more cooling channels containing a cooling medium.

8. The ultrasound transducer device according to claim 7, wherein the at least one carrier element is composed of two plates which are structured such that the one or more cooling channels are formed at their joined surfaces.

9. The ultrasound transducer device according to claim 8, wherein the at least one carrier element forms a heat pipe system enclosed on all sides, with a corresponding cooling medium in its one or more cooling channels.

10. The ultrasound transducer device according to claim 7, wherein the at least one carrier element forms a heat pipe system enclosed on all sides, with a corresponding cooling medium in its one or more cooling channels.

11. The ultrasound transducer device according to claim 1, further comprising means for enlarging a heat exchanger surface on at least one outside surface of at least one carrier element.

12. The ultrasound transducer device according to claim 1, wherein at least one carrier element of the device is extended into an extension part in a longitudinal direction beyond a region of its electronic circuit portion.

13. The ultrasound transducer device according to claim 12, wherein said transducer elements are arranged in an array such that adjacent carrier elements are arranged in an arrangement offset from one another in such a way that extension parts of the adjacent carrier elements form cooling ribs for an external cooling medium.

14. The ultrasound transducer device according to claim 1, wherein at least one carrier element is composed at least partially of silicon (Si).

15. The ultrasound transducer device according to claim 14, wherein at least one electronic circuit portion is integrated at least partially into the silicon of the carrier element.

16. The ultrasound transducer device according to claim 1, wherein the electronic circuit portion contains separate electronic parts for transmission and reception.

17. The ultrasound transducer device according to claim 1, wherein the transducer elements of at least one row have a common electrode at end faces of their oscillation elements.

18. The ultrasound transducer device according to claim 1, wherein an array of said transducer elements is a one-dimensional array of transducer elements.

19. The ultrasound transducer device according to claim 1, wherein an array of said transducer elements is a two-dimensional array of transducer elements.

* * * * *